United States Patent
Ruech et al.

(10) Patent No.: US 8,673,158 B2
(45) Date of Patent: Mar. 18, 2014

(54) PROCESS FOR CLEANING WASTEWATERS FROM MELAMINE PLANTS

(75) Inventors: Wolfgang Ruech, Taiskirchen (AT); Christoph Neumüller, Ennsdorf (AT); Thomas Wallek, Steyr (AT)

(73) Assignee: AMI Agrolinz Melamine International GmbH, Linz (AT)

( * ) Notice: Subject to any disclaimer, the term of this patent is extended or adjusted under 35 U.S.C. 154(b) by 947 days.

(21) Appl. No.: 11/921,990

(22) PCT Filed: Jun. 13, 2006

(86) PCT No.: PCT/EP2006/005847
§ 371 (c)(1),
(2), (4) Date: Aug. 12, 2009

(87) PCT Pub. No.: WO2006/133966
PCT Pub. Date: Dec. 21, 2006

(65) Prior Publication Data
US 2009/0294272 A1    Dec. 3, 2009

(30) Foreign Application Priority Data
Jun. 15, 2005 (DE) .................... 10 2005 028 665

(51) Int. Cl.
*C02F 1/04* (2006.01)

(52) U.S. Cl.
USPC .............. 210/774; 210/767; 203/24; 423/358

(58) Field of Classification Search
USPC ......................................................... 203/24
See application file for complete search history.

(56) References Cited

U.S. PATENT DOCUMENTS

| 2,423,411 | A |   | 7/1947  | Simpson              |
|-----------|---|---|---------|----------------------|
| 3,496,176 | A |   | 2/1970  | Kennedy              |
| 4,013,757 | A |   | 3/1977  | Berkowitz et al.     |
| 4,308,385 | A |   | 12/1981 | Goorden              |
| 4,408,046 | A | * | 10/1983 | Van Hardeveld ...... 544/201 |
| 4,565,867 | A |   | 1/1986  | Thomas et al.        |

(Continued)

FOREIGN PATENT DOCUMENTS

DD    150601 A5    9/1981
DE   1930844 A1    1/1970

(Continued)

OTHER PUBLICATIONS

Xinglong Liu and Xuefeng Fu; "Simulative Calculation on Two Wastewater Treatment Equipments"; Sichuan Chemical Co., Ltd.; Feb. 15, 2005.

*Primary Examiner* — John Kim
(74) *Attorney, Agent, or Firm* — The Webb Law Firm

(57) ABSTRACT

The invention relates to a method for purifying wastewaters of melamine systems. The method is characterized in that triazine-containing wastewater is subjected to a thermal pretreatment stage, whereupon the vapors are condensed from the gas phase of the thermal pretreatment stage, and the liquid phase of the thermal pretreatment stage is subjected to a thermal hydrolysis stage while $NH_3$ is isolated from the obtained liquid phase containing $H_2O$, $CO_2$, and $NH_3$. The inventive method makes it possible to compensate varying wastewater qualities, thus allowing the melamine system and wastewater station to be operated in a constant and safe fashion. Furthermore, the strain on the subsequent thermal hydrolysis stage is relieved with the aid of the thermal pretreatment stage of the inventive method.

17 Claims, 1 Drawing Sheet

(56) References Cited

U.S. PATENT DOCUMENTS

| | | |
|---|---|---|
| 4,663,387 A | 5/1987 | Lahalih et al. |
| 5,514,796 A | 5/1996 | Best et al. |
| 2006/0011560 A1 | 1/2006 | Ruech et al. |

FOREIGN PATENT DOCUMENTS

| | | |
|---|---|---|
| DE | 2616054 A1 | 10/1976 |
| DE | 10229103 A1 | 1/2004 |
| EP | 0019326 A1 | 11/1980 |
| IT | 01282369 | 1/1996 |
| IT | 01282370 | 1/1996 |
| RU | 2161608 C2 | 1/2001 |
| WO | 0146159 A2 | 6/2001 |
| WO | 02081379 A1 | 10/2002 |

* cited by examiner

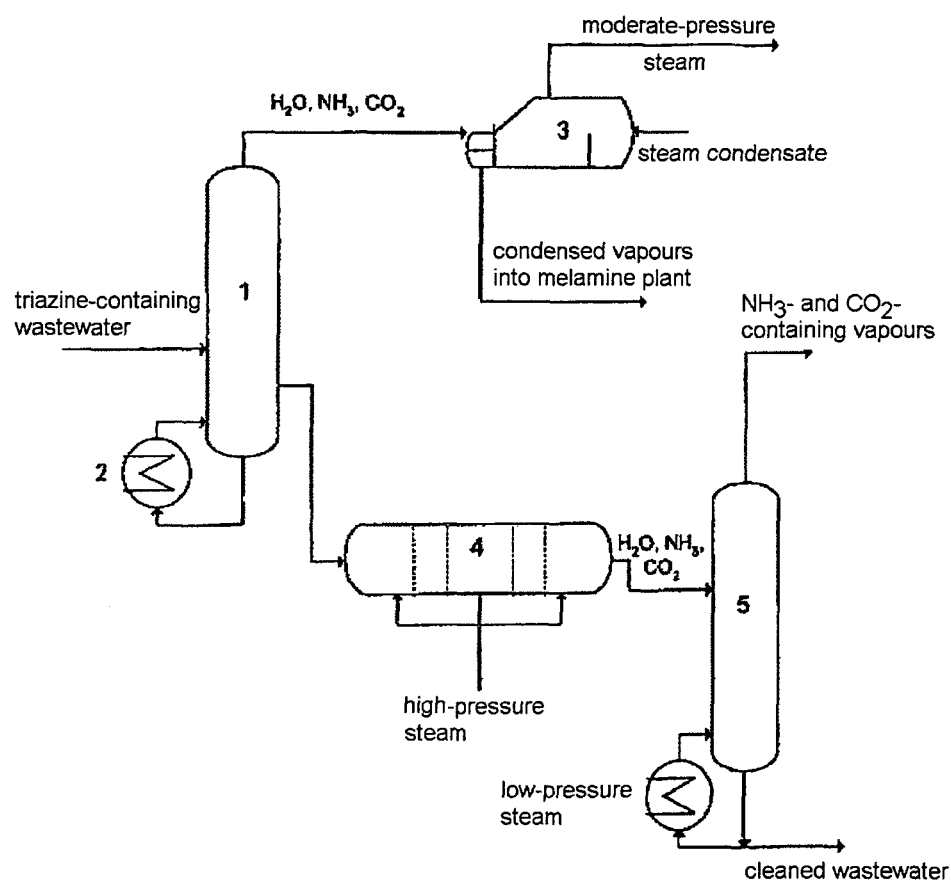

PROCESS FOR CLEANING WASTEWATERS FROM MELAMINE PLANTS

BACKGROUND OF THE INVENTION

1.) Field Of The Invention

The present invention relates to a process for cleaning wastewaters from melamine plants and to an apparatus for the same.

2.) Description of the Related Art

Melamine is prepared almost exclusively from urea by the following reaction equation:

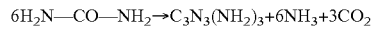

$$6H_2N-CO-NH_2 \rightarrow C_3N_3(NH_2)_3 + 6NH_3 + 3CO_2$$

The melamine preparation process can be divided into two categories. There are noncatalytic high-pressure processes in which the melamine is prepared in the liquid phase at pressures of >70 bar. In the catalytic low-pressure processes, melamine is synthesized at approximately atmospheric pressure in the gas phase.

What is common to all melamine processes is that the crude melamine from the synthesis stage then has to be purified, since it comprises by-products. To degrade the by-products, the crude melamine is usually worked up in the presence of water, since the by-products go into solution in water under certain conditions. In this way, wastewaters contaminated with nitrogen-containing substances occur at various stages of the melamine plant. These wastewater ingredients are mainly cyclic nitrogen compounds in the form of triazines such as melamine, ureidomelamine, cyanuric acid or oxoamino-triazines (OATs) such as ammeline or ammelide. In addition, depending on the plant status, varying amounts of acyclic nitrogen compounds, for example urea, or else carbonates and sodium or ammonium ions may be present.

The wastewaters contaminated in this way have to be treated to remove their ingredients before they can be discharged.

One example of the wastewater treatment of a melamine process is described by WO 01/46159 A2. According to this, the triazine-contaminated mother liquor obtained in the crystallization of the melamine from aqueous solution is acidified, which crystallizes out the OATs. The OAT suspension thus obtained is subjected to a tangential filtration in which melamine-rich permeate and an OAT suspension as the retentate are obtained. While the melamine-rich permeate is recycled into the plant, the OATs are removed from the retentate. This process has the disadvantage that it is complicated, and the precipitated OATs additionally have to be disposed of.

A further means of wastewater treatment in melamine plants consists in treating the wastewaters in a thermal wastewater treatment plant (TAA), where the triazine-containing wastewater ingredients are hydrolysed under high pressure and high temperature in the liquid phase to $CO_2$ and $NH_3$. Such a process is described, for example, in IT 01282370. There, the crystallization mother liquors of a melamine plant are heated to 180 to 250° C. in a closed vessel under the autogenous pressure of the system and left for 20 to 120 min, as a result of which the melamine and OAT ingredients are degraded.

In a similar manner, according to IT 0128369, triazine-containing melamine wastewater is treated in a closed vessel at a temperature of >250° C. The $NH_3$ and $CO_2$ formed is subsequently stripped off and the resulting pure liquid is recycled into the plant or discharged.

According to DE 102 29 103 A1, the triazine-containing wastewater of a melamine plant is passed in a meandering flow through a heatable apparatus. At temperatures of >190° C. and the system equilibrium pressure, which is about 30 to 60 bar, the wastewater ingredients are decomposed to $NH_3$ and $CO_2$. The reaction takes place in the liquid phase, but small evaporation losses cannot be prevented.

What is common to the processes mentioned is that they are one-stage processes whose hydrolysis apparatus, with regard to pressure, temperature and residence time, is designed for a certain, constant quality and amount of wastewater. In normal operation of the plant, the desired degrees of degradation of the ingredients are thus achieved. However, as soon as operating states occur in which the wastewater varies with regard to concentration and type of ingredients, the required degrees of degradation can no longer be ensured.

SUMMARY OF THE INVENTION

It is an object of the invention to find a process for cleaning wastewaters of a melamine plant, which does not have the disadvantages detailed.

BRIEF DESCRIPTION OF THE FIGURE

FIG. 1 illustrates one embodiment of the process according to the present invention.

DETAILED DESCRIPTION OF THE PREFERRED EMBODIMENTS

The present invention provides a process for cleaning wastewaters of a melamine plant, which is characterized in that triazine-containing wastewater is subjected to a thermal pretreatment stage to form a gas phase and a liquid phase, then the vapours from the gas phase of the thermal pretreatment stage are condensed, and the liquid phase of the thermal pretreatment stage is subjected to a thermal hydrolysis stage and $NH_3$ is removed from the resulting $H_2O$—, $CO_2$— and $NH_3$-containing liquid phase.

The advantage of the inventive two-stage wastewater cleaning process is that the thermal pretreatment stage allows varying plant states in which different wastewater qualities occur to be compensated for. In the thermal pretreatment stage, certain wastewater ingredients, for instance urea, are already decomposed substantially to $NH_3$ and $CO_2$. Such urea-contaminated wastewaters occur, for instance, in the course of start-up or else shut-down operations of the melamine plant. When such wastewaters are conducted directly into a thermal wastewater hydrolysis without a pretreatment stage, the operating mode of the entire plant has to be adjusted exactly to the changed conditions in order to be able to ensure the desired degree of degradation of the wastewater ingredients. This entails a high level of control and monitoring complexity in all situations deviating from normal operation.

The thermal pretreatment stage connected upstream of the wastewater hydrolysis in accordance with the invention surprisingly makes it possible to compensate for varying wastewater qualities to such an extent that the wastewater in the feed to the thermal hydrolysis always has a substantially identical quality virtually irrespective of the plant status. This allows a constant and safe operating mode of the melamine plant and of the wastewater plant.

A further advantage of the process according to the invention in that, in the thermal pretreatment stage, the cyclic nitrogen compounds are already degraded partly, so that lower residence times are necessary for the residual degradation in the subsequent hydrolysis stage.

Thus, advantageously, at least 15% by weight of the wastewater is converted in the thermal pretreatment to an $H_2O$—, $CO_2$— and $NH_3$-containing gas phase and worked up separately, so that the subsequent hydrolysis stage is also deburdened with regard to its hydraulic amount to be processed. The remaining portion of the wastewater is obtained as a triazine-containing liquid phase.

Typically, the wastewater of a melamine plant comprises triazines, for instance the oxoaminotriazines ammeline and ammelide, melamine, melam, cyanomelamine, ureidomelamine, cyanuric acid, and also ammonia, carbon dioxide, urea and possibly NaOH in different amounts.

The wastewater stems for the most part from the melamine crystallization and the melamine filtration of the melamine plant and advantageously has the pH values and temperatures existing there. Preference is given to wastewater temperatures of up to about 60° C. and pH values of about 12. The wastewater is also advantageously preheated to about 150 to 250° C. before it enters the thermal pretreatment stage.

It is preferred when the wastewater stems from a vacuum crystallization and a melamine filtration. It is particularly preferred when the wastewater stems from a mother liquor crystallization downstream of a vacuum crystallization. In the mother liquor crystallization, the melamine still present is substantially crystallized out of the mother liquor of the melamine crystallization. It is only the virtually melamine-free solution obtained there that passes into the wastewater plant and is decontaminated by it.

The temperatures and pressures in the thermal pre-treatment stage may vary within wide ranges. While the temperature is established via the type and amount of the heat carrier, the pressure in the apparatus is dependent upon the reaction rate of the evaporation and degradation reactions as they proceed, and upon the vapour pressure of the reaction products.

Preferably, the temperature in the thermal pretreatment stage is 140 to 250° C., more preferably 180 to 220° C.

Also with preference, the pressure in the thermal pre-treatment stage is 5 to 50 bar, more preferably 15 to 30 bar.

Under these conditions, both the evaporation of the wastewater and the degradation of the individual ingredients proceeds so efficiently that the apparatus size can be kept within sensible limits. The pressure and temperature conditions can also be used to optimize the heat recovery from the vapours of the thermal pretreatment stage, for example in the form of steam, in a location-specific manner.

Preferably, the heat carrier used is steam, preferably high-pressure steam. Steam is available in a sufficient amount in every melamine plant, and it is possible to use steam of any pressure level, even, for instance, in the form of moderate- or low-pressure steam.

A main objective of the thermal pretreatment stage is the compensation for different wastewater qualities by the degradation of certain ingredients which occur especially in the event of exceptional operating states of the melamine plant. These ingredients are often acyclic nitrogen compounds, for instance urea, which occurs to an enhanced degree in the course of start-up and shut-down operations. It is therefore advantageous when the triazine-containing liquid phase, after the thermal pretreatment stage, now has only <1% by weight, more preferably 0.5% by weight, of acyclic nitrogen compounds. In this way, the subsequent thermal hydrolysis stage is deburdened in material terms to such an extent that it can be operated virtually always under constant conditions.

It is advantageous when the residence time of the triazine-containing wastewater in the thermal pretreatment stage is 0.5 to 2 h, more preferably 1 to 1.5.

In parallel to the degradation of wastewater ingredients, the conversion of a portion of the waste-water into the gas phase takes place in the thermal pretreatment stage. The higher the fraction of wastewater converted to the gas phase, the more advantageous this is. A high gas phase content means that large amounts of water are evaporated out of the wastewater and that many by-products are degraded as early as in the pretreatment stage. Preferably, at least 50% by weight of the wastewater is obtained as an $H_2O$—, $CO_2$— and $NH_3$-containing gas phase. In this way, it is possible for both the hydraulic and the material loading for the subsequent thermal hydrolysis stage to be reduced significantly.

The gas phase formed in the thermal pretreatment stage is drawn off and the vapours are condensed. As this is done, heat is advantageously recovered in the form of steam. Depending on what steam quality is utilizable at the location, it is possible, for example, to recover moderate-pressure steam or low-pressure steam and recycle it into the melamine plant. This heat recovery improves the overall steam balance of the melamine plant.

The condensed vapours of the thermal pretreatment stage consist substantially of $H_2O$, $CO_2$ and $NH_3$. They can be recycled into the urea plant or into the melamine plant.

Preferably, $CO_2$ and $NH_3$ are removed from the condensed vapours. This can be done by means of known methods, for example by stripping with steam. Pure water is obtained, which can be recycled as process condensate into the melamine plant. In this way, at least a portion of the fresh water required can be saved.

Owing to the evaporation of water and the degradation of a portion of the ingredients, the liquid phase obtained in the thermal pretreatment stage comprises virtually exclusively compounds which are difficult to degrade. These are in particular the triazines in the form of the OATs ammeline and ammelide, and also melamine.

This triazine-containing liquid phase is fed to a thermal hydrolysis stage in which the triazines are degraded substantially in the liquid phase, at high pressure and high temperature, to give $H_2O$, $CO_2$ and $NH_3$.

Preferably, the thermal hydrolysis takes place at a temperature of 200 to 260° C. and a pressure of 30 to 100 bar. Typically, the temperature of the thermal hydrolysis stage is higher than the temperature of the thermal pretreatment stage, so that heat has to be supplied to the OAT triazine-containing liquid phase for the hydrolysis. This is done, for example, by the supply of steam as a heat carrier into the hydrolysis apparatus, the heat typically being transferred in indirect form.

The higher the temperature is in the thermal hydrolysis stage, the more rapidly the degradation of the waste-water ingredients proceeds and the higher the pressure that is needed to keep the reaction mixture in the liquid phase.

The thermal hydrolysis preferably takes place in at least one horizontal apparatus. An advantageous variant of a thermal hydrolysis stage and of the hydrolysis apparatus is described, for example, in DE 102 29 103 A1. It is also possible to use a plurality of apparatuses in series for the thermal hydrolysis.

In the thermal hydrolysis stage, an $H_2O$—, $CO_2$— and $NH_3$-containing liquid phase is obtained. $NH_3$ is advantageously removed from this liquid by stripping with steam, so that $NH_3$-free $H_2O$ can be removed at the bottom of the stripper. The $NH_3$-rich vapours are returned into the melamine plant or into the urea plant.

In the specific case that the aqueous workup part of the melamine plant proceeds in the presence of NaOH, the $H_2O$-rich phase bottom is discharged; it comprises, inter alia, sodium carbonate and therefore cannot be recycled into the melamine process.

The invention also provides an apparatus for performing the process according to the invention.

The apparatus has
at least one apparatus for thermal pretreatment having an internal or external heat exchanger and a separation apparatus,
at least one apparatus for condensation of the vapours from the thermal pretreatment stage,
at least one apparatus for thermal hydrolysis,
at least one apparatus for removing $NH_3$ from the liquid phase of the thermal hydrolysis stage.

The present purification process allows the wastewater of any desired melamine process to be purified in a simple and efficient manner.

FIGURE 1 shows, by way of example, one embodiment of the process according to the invention.

Triazine-containing wastewater of a melamine plant is fed to a thermal pretreatment stage 1 with an external heat exchanger 2. An $H_2O$—, $NH_3$— and $CO_2$-containing gas phase is drawn off from the thermal pre-treatment stage 1 and is condensed in the steam generator 3 with the aid of steam condensate. This affords moderate-pressure steam which is recycled into the melamine plant.

The liquid phase of the thermal pretreatment stage 1 passes into the thermal hydrolysis 4, where the waste-water ingredients are degraded with the aid of high-pressure steam in a horizontal hydrolysis apparatus. The $H_2O$—; $CO_2$— and $NH_3$-containing liquid phase is fed to a wastewater stripper 5, where $NH_3$ and $CO_2$ are driven out by stripping with low-pressure steam. In the bottom of the wastewater stripper 5, cleaned wastewater is obtained.

The invention will be illustrated hereinbelow with reference to examples; the accompanying measurements are shown in Table 1.

In the comparative example, wastewater containing triazine and 4.0% by weight of urea from a melamine plant is introduced without a thermal pretreatment stage into a thermal hydrolysis stage which is operated at a temperature of 240° C. and a pressure of 45 bar. The reaction mixture in the hydrolysis apparatus contains 4% by weight of $NH_3$, 5.4% by weight of $CO_2$ and 90.6% by weight of $H_2O$. 20% by weight of the reaction mixture is present in gaseous form, a considerable part of the gas phase being caused by the hydrolysis of the urea.

In order to be able to keep the pressure in the hydrolysis apparatus constant, the gas phase has to be removed. This means that continuous evaporation takes place. A disadvantage in this context is that the formation of gas bubbles considerably reduces the actual reaction volume for the degradation reaction and thus worsens the degradation of the wastewater ingredients.

Alternatively to the removal of the gas phase, the pressure can be maintained by lowering the temperature in the apparatus, in order to keep the gas phase fraction smaller. As a result, however, the reaction rates are reduced, so that long residence times are needed in order to achieve the desired degree of degradation of the triazines.

In Example 1, the same triazine- and urea-containing wastewater as in the comparative example is subjected in accordance with the invention first to a thermal pretreatment stage and then to a thermal hydrolysis stage. The thermal pretreatment takes place at a temperature of 200° C., a pressure of 22 bar for a residence time of 1 h. In the course of the thermal pretreatment, 40% by weight of the total amount of wastewater is evaporated. The majority of the urea present in the wastewater is degraded here and removed in the form of $NH_3$ and $CO_2$. The remaining liquid phase, which corresponds to a hydraulic amount of 60% by weight of the total amount of wastewater, contains only 2% by weight of urea. It is subjected to a thermal hydrolysis stage under the same temperature and pressure conditions as in the comparative example. The reaction mixture in the hydrolysis apparatus contains 1.7% by weight of $NH_3$, 1.1% by weight of $CO_2$ and 97.3% by weight of $H_2O$. This corresponds to a gas phase fraction of 2.3% by weight. This means that only a very low level of evaporation occurs and hence the temperature and pressure conditions in the hydrolysis apparatus can be kept constant. This leads to the desired high degradation rates of the wastewater ingredients.

COMPARATIVE EXAMPLE

Thermal Hydrolysis

| Reaction mixture in thermal hydrolysis stage | | |
|---|---|---|
| $NH_3$ | [% by wt.] | 4.0% |
| $CO_2$ | [% by wt.] | 5.4% |
| $H_2O$ | [% by wt.] | 90.6% |
| Temperature | [° C.] | 240 |
| Pressure | [bar] | 45 |
| Gas phase fraction | [% by wt.] | 20% |

EXAMPLE 1

Thermal Pretreatment with Downstream Hydrolysis

| Reaction mixture in thermal hydrolysis stage | | |
|---|---|---|
| $NH_3$ | [% by wt.] | 1.7% |
| $CO_2$ | [% by wt.] | 1.1% |
| $H_2O$ | [% by wt.] | 97.3% |
| Temperature | [° C.] | 240 |
| Pressure | [bar] | 45 |
| Gas phase fraction | [% by wt.] | 2.3% |

Reference Numeral List
1 Thermal pretreatment
2 Heat exchanger
3 Steam generator
4 Thermal hydrolysis
5 Wastewater stripper

The invention claimed is:
1. A process for cleaning wastewaters of a melamine plant, comprising the steps of:
subjecting liquid triazine-containing wastewater to a thermal pretreatment stage to form a $H_2O$—, $CO_2$—, and $NH_3$— containing gas phase and a liquid phase, wherein the temperature in the thermal pretreatment stage is 140 to 250° C., and wherein the pressure in the thermal pretreatment stage is 15 to 30 bar, then
separating the $H_2O$—, $CO_2$—, and $NH_3$— containing gas phase from the liquid phase, condensing the vapors from the $H_2O$—, $CO_2$—, and $NH_3$— containing gas phase of the thermal pretreatment stage, and subjecting the liquid phase of the thermal pretreatment stage to a thermal hydrolysis stage and removing $NH_3$ from the resulting $H_2O$—, $CO_2$—, and $NH_3$— containing liquid phase.

2. The process according to claim 1, wherein at least 15% by weight of the liquid triazine-containing wastewater is obtained in the thermal pretreatment stage as $H_2O$—, $CO_2$— and $NH_3$— containing gas phase, and the remaining portion of the liquid triazine-containing wastewater as triazine-containing liquid phase.

3. The process according to claim 1, wherein the liquid triazine-containing wastewater stems from a vacuum crystallization and a melamine filtration.

4. The process according to claim 1, wherein the liquid triazine-containing wastewater stems from a mother liquor crystallization downstream of a vacuum crystallization.

5. The process according to claim 1, wherein the temperature in the thermal pretreatment stage is 180 to 220° C.

6. The process according to claim 1, wherein steam is fed to the thermal pretreatment stage as a heat carrier.

7. The process according to claim 1, wherein the triazine-containing liquid phase from the thermal pretreatment stage has <1% by weight of acyclic nitrogen compounds.

8. The process according to claim 7, wherein the triazine-containing liquid phase from the thermal pretreatment stage has <0.5% by weight of acyclic nitrogen compounds.

9. The process according to claim 1, wherein the residence time of the triazine-containing wastewater in the thermal pretreatment stage is 0.5 to 2 h.

10. The process according to claim 9, wherein the residence time of the triazine-containing wastewater in the thermal pretreatment stage is 1 to 1.5 h.

11. The process according to claim 1, wherein at least 50% by weight of the liquid triazine-containing wastewater is obtained in the thermal pretreatment stage as $H_2O$—, $CO_2$— and $NH_3$— containing gas phase.

12. The process according to claim 1, wherein heat is recovered in the vapor condensation in the form of steam and the steam is recycled into the melamine plant.

13. The process according to claim 1, wherein $CO_2$ and $NH_3$ are removed from the condensed vapors of the thermal pretreatment stage by stripping with steam and the resulting water is recycled into the melamine plant.

14. The process according to claim 1, wherein the thermal hydrolysis stage proceeds at a temperature of 200 to 260° C.

15. The process according to claim 1, wherein the thermal hydrolysis stage proceeds at a pressure of 30 to 100 bar.

16. The process according to claim 1, wherein a thermal hydrolysis stage proceeds in at least one horizontal apparatus.

17. The process according to claim 1, wherein $NH_3$ is removed by stripping with steam from the $H_2O$—, $CO_2$— and $NH_3$— containing liquid phase of the thermal hydrolysis stage and $NH_3$— free $H_2O$ is drawn off at the bottom of the stripper.

* * * * *

UNITED STATES PATENT AND TRADEMARK OFFICE
CERTIFICATE OF CORRECTION

PATENT NO. : 8,673,158 B2  Page 1 of 1
APPLICATION NO. : 11/921990
DATED : March 18, 2014
INVENTOR(S) : Ruech et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1731 days.

Signed and Sealed this

Twenty-ninth Day of September, 2015

Michelle K. Lee
*Director of the United States Patent and Trademark Office*